United States Patent
Uenluebayir et al.

(10) Patent No.: US 8,143,908 B2
(45) Date of Patent: Mar. 27, 2012

(54) BIOSENSOR AND A METHOD OF MEASURING A CONCENTRATION OF AN ANALYTE WITHIN A MEDIUM

(75) Inventors: Sinan Uenluebayir, Bochum (DE); Hoc-Khiem Trieu, Kamp-Lintfort (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 740 days.

(21) Appl. No.: 12/208,491

(22) Filed: Sep. 11, 2008

(65) Prior Publication Data

US 2009/0066347 A1    Mar. 12, 2009

(30) Foreign Application Priority Data

Sep. 11, 2007 (DE) .......................... 10 2007 043 132

(51) Int. Cl.
*G01R 27/08* (2006.01)
*G01N 27/414* (2006.01)

(52) U.S. Cl. .................................. 324/691; 204/403.01
(58) Field of Classification Search .................. 324/691; 204/400–435; 205/775–794.5
See application file for complete search history.

(56) References Cited

U.S. PATENT DOCUMENTS

| | | | | |
|---|---|---|---|---|
| 5,234,566 A | * | 8/1993 | Osman et al. | 204/403.06 |
| 5,466,348 A | * | 11/1995 | Holm-Kennedy | 205/775 |
| 5,567,301 A | * | 10/1996 | Stetter et al. | 205/777.5 |
| 6,133,741 A | * | 10/2000 | Mattes et al. | 324/502 |
| 6,424,174 B1 | * | 7/2002 | Nowak et al. | 326/81 |
| 6,440,662 B1 | | 8/2002 | Gerwen et al. | |
| 6,846,654 B1 | * | 1/2005 | Blackburn et al. | 435/7.1 |
| 7,693,561 B2 | | 4/2010 | Schrepfer et al. | |
| 2005/0230271 A1 | | 10/2005 | Levon et al. | |
| 2006/0016699 A1 | | 1/2006 | Kamahori et al. | |
| 2006/0278528 A1 | | 12/2006 | Fleischer et al. | |
| 2007/0095664 A1 | * | 5/2007 | Chou et al. | 204/433 |
| 2007/0132043 A1 | * | 6/2007 | Bradley et al. | 257/414 |
| 2010/0270174 A1 | * | 10/2010 | Chen et al. | 205/777.5 |

FOREIGN PATENT DOCUMENTS

| | | |
|---|---|---|
| DE | 4006908 C1 | 6/1991 |
| DE | 10255755 A1 | 7/2004 |
| DE | 69632921 T2 | 7/2005 |
| DE | 60124714 T2 | 8/2007 |
| WO | 2004/040291 A1 | 5/2004 |

OTHER PUBLICATIONS

Gibilisco, The Illustrated Dictionary of Electronics, New York McGraw-Hill Professional, 2001.*
Sherman, Measure resistance and capacitance without an A/D, Philips Semiconductors Microcontroller Products, 1993.*

* cited by examiner

*Primary Examiner* — Melissa Koval
*Assistant Examiner* — Daniel Miller
(74) *Attorney, Agent, or Firm* — Keating & Bennett, LLP (57) ABSTRACT

A biosensor for measuring a concentration of an analyte within a medium includes an electrical charge storage and a resistive layer including an electrical resistance which changes upon contact with the analyte. The electrical charge storage includes a sensor electrode, and the resistive layer may be contacted with the medium and is arranged between the medium and the sensor electrode such that during contact with the medium, a number of the electrical charges stored in the electrical charge storage pass the resistive layer.

28 Claims, 5 Drawing Sheets

BIOSENSOR AND A METHOD OF MEASURING A CONCENTRATION OF AN ANALYTE WITHIN A MEDIUM

CROSS-REFERENCE TO RELATED APPLICATIONS

This application claims priority from German Patent Application No. 102007043132.7, which was filed on Sep. 11, 2007, and is incorporated herein in its entirety by reference.

BACKGROUND OF THE INVENTION

The present invention relates to a biosensor and to a method of measuring a concentration of an analyte within a medium, and in particular to an ultra-sensitive CMOS biosensor, it being possible to use the sensor for detecting minute quantities of an analyte within a solution.

Biosensors comprising a biological component and a physical signal transducer are mainly designed for analytical purposes such as clinical analysis, quality control of foodstuff and analyses of environmental pollution. A problem associated with biosensors or sensors in general consists in implementing a sensor which comprises high selectivity and high sensitivity at the same time. Both requirements are the result of fields of application of biosensors, which for example comprise detecting tumor markers in blood serum of down to a detection threshold of $10^{-13}$ mol/liter in the presence of many other constituents in the blood. Only few of the currently employed biosensors or analysis systems (assays) reach such a low detection limit or are time-consuming and complicated to use. In addition, many of the conventional biosensors/assays cannot be miniaturized for fundamental reasons, and therefore cannot be integrated into portable analytical equipment.

Generally, a biosensor comprises two essential functional units. Firstly, they include a biological detection module comprising biologically sensitive material, and secondly, they include the signal transducer providing the detection signal. A multitude of receptor molecules may be used for the biological detection module. Examples of this are enzymes, antibodies, ligands, receptors, peptides, oligonucleotides, cells of organs, organisms or pieces of tissue.

Current biosensors are based on a multitude of principles, and classification may be performed by their transduction mechanisms. According to this, one differentiates, for example, between chemical, optical and physical biosensors. Chemical biosensors, again, are subdivided into amperometric, potentiometric and conductometric biosensors. With regard to optical biosensors, various optical properties such as absorption, fluorescence/phosphorescence, bio/chemiluminescence, reflectivity, light scattering and reflection index are exploited, this list being an exemplary list only. Physical detection methods include, for example, microgravimetric and calorimetric biosensors.

An important subgroup of biosensors includes sensors based on immunological mechanisms. In this context, the affinity reaction between antigen and associated antibody is exploited, for example, for detecting an analyte. By combining the specific and sensitive antigen-antibody binding reaction with highly sensitive analytical, mostly optical methods, a multitude of different biosensors have been realized. Recombinant antibody production, which enables creation of antibodies for many antigens, further enables realizing so-called immunosensors, which may be applied for detecting a broad spectrum of antibodies.

Conventional biosensors utilizing this principle are described, for example, in US 2006/0016699 A1, US 2005/0230271 A1, DE 102 55 755 B4 and WO 2004/040291 A1. In these sensors, a change in the electrical characteristic of a field-effect transistor resulting from the analyte binding to the gate is detected. EP 1 715 333 A2 further discloses a method of signal reading and a gas-sensitive field-effect transistor, an air gap being arranged between the gate electrode with a gas-sensitive layer. DE 4006908 C1 finally discloses an ion-sensitive sensor comprising a floating gate, the floating gate being connected to a sensor face, so that ions impinging on the sensor face result in a detectable signal (change in a capacitance).

One important evaluation criterion for biosensors is their ease of applicability in practice and in addition the possibility of miniaturization, which is especially important particular for using portable systems. In this context, biosensors based on electrochemical principles generally have greater advantages over optical biosensors.

Even though there are thus a multitude of biosensors for very different fields of application, there is neither one universal sensor for a broad spectrum of tasks, nor does there exist, for each task, an easy-to-handle sensor which is highly sensitive, on the one hand, and offers a broad potential for miniaturization, on the other hand.

SUMMARY

According to an embodiment, a biosensor for measuring a concentration of an analyte within a medium may have: an electrical charge storage, the electrical charge storage including a sensor electrode; and a resistive layer including an electrical resistance which changes upon contact with the analyte, wherein the resistive layer may be contacted with the medium and is arranged between the medium and the sensor electrode such that during contact with the medium, a number of the electrical charges stored in the electrical charge storage pass the resistive layer.

According to another embodiment, a method of producing a biosensor for measuring a concentration of an analyte within a medium may have the steps of: providing a charge storage including a sensor electrode; and applying a resistive layer including an electrical resistance which changes upon contact with the analyte, the resistive layer being arranged such that it may be contacted with the medium and is arranged between the medium and the sensor electrode such that during contact with the medium, a number of electrical charges pass through the resistive layer.

According to another embodiment, a method of measuring a concentration of an analyte within a medium which may be contacted with a resistive layer may have the steps of: charging an electrical charge storage by means of an electrical supply, when the medium including the analyte is in contact with the resistive layer; disconnecting the sensor electrode from the electrical supply; discharge of electrical charges through the resistive layer into the medium; and detecting a remaining charge quantity on the sensor electrode after a predetermined time period.

The present invention is based on the finding that a biosensor for measuring a concentration of an analyte within a medium may be provided in that a charge-storing device, which comprises a sensor electrode, and an integrated selective membrane are combined such that charges may leak off from the sensor electrode via the integrated selective membrane when it comes into contact with the medium. The integrated selective membrane is arranged, for example, between the medium and the sensor electrode, and has an electrical resistance which changes upon contact with the analyte, so that the concentration is determined by the amount of charges passing the integrated selective membrane.

Thus, embodiments of the present invention are based, as a functional principle, on a so-called leakage sensor. The principle of a leakage sensor is based on that initially, electrical charge is stored, and subsequently, a detection signal is generated by the stored charges leaking off. Generally, leaking off of the charge is extremely slow and is therefore often not directly detectable. However, measurement may be performed over a relatively long time period, so that even with very small amounts of charge leaking away per time unit, a measurable effect may be determined.

Such a leakage sensor may be realized, for example, by means of a capacitor, a capacitor electrode serving as a sensor electrode which is isolated from the medium comprising the analyte by a deposited membrane (integrated selective membrane) or a coating. A reference electrode, for example, may be located within the medium, so that at a potential difference, a current may form from the sensor electrode via the membrane to the reference electrode.

In particular, embodiments of the present invention exploit the fact that the conductivity of the (suitably selected) membrane changes upon attachment or docking of an analyte, and that as a result, the leakage of charge from the capacitor changes. So as to be able to detect a specific analyte within a matrix (e.g. an aqueous solution), for example, the membrane comprises selective binding sites for the analyte to be detected. Any kind of coating which changes the electrical conductivity selectively relative to the analyte within question, on the one hand, and in the presence of the analyte, on the other hand, may be used as the membrane (sensitive sensor layer or selective membrane). Therefore, the membrane will also be referred to as a resistive layer below, the change in the conductivity, or the change in the resistance, amounting to at least 5% or 10% or at least 20% or at least 50%. Simultaneously with the change in the electrical conductivity, the leakage rate of the charge stored on the storing element is also changed. The difference between the charge prior to and after binding or docking of analyte molecules therefore is a measure of the analyte concentration within the matrix contemplated.

Any measured quantity reflecting the state of charge of the electrical charge storage (charge-storing element) may be used as the sensor signal. For example, this may be a voltage or a charging or discharging current for the case of a capacitor which is contemplated here. In addition to using the capacitor, further charge-storing devices may also be used for the inventive concept (measuring a leakage rate of charge).

However, the inventive concept of a potential measuring procedure shall be described below while using a capacitor as the charge storage. The capacitor, which comprises a capacitance C, initially is to be charged with an output voltage $U_0$. In the event that the sensitive membrane is not in contact with the analyte (medium without analyte), the resistance of the membrane via which the capacitor may discharge shall have a value of $R_0$. Thus, the voltage present at the capacitor after a time t is therefore given by $$U = U_0 \cdot e^{-\frac{t}{R_0 \cdot C}}. \tag{1}$$

After a discharge, the capacitor may be charged again with the voltage $U_0$. However, if the sensitive membrane is in contact with an analyte, the value of the resistance will change. After a while, a constant changed resistance value $R_A$ for the sensitive membrane will arise, and a new equilibrium state will have formed. The resistance value or leakage resistance $R_A$, which is constant in time, generally depends on the concentration of the analyte—at least when the sensitive membrane is suitably selected. By analogy with the case that no analyte is present, the voltage at the capacitor will amount to $$U_A = U_0 \cdot e^{-\frac{t}{R_A \cdot C}} \tag{2}$$

after a time t in the event that an analyte is present.

Combining both equations will result in $$\frac{U_A}{U} = e^{\frac{t}{R_0 \cdot C}\left(1 - \frac{R_0}{R_A}\right)}, \tag{3}$$

it being possible for t to be a predetermined time or time interval. Therefore, the ratio of the voltages for both cases that an analyte is or is not present, is therefore determined by the ratio of the resistances $R_0$ and $R_A$ for the two respective cases.

In a further embodiment, the capacitor may be replaced by an EPROM (erasable programmable read-only memory), and/or the charge leakage may be detected by a so-called floating gate. A floating gate is a gate contact or a control contact, for example for a field-effect transistor (FET), the potential present at the control contact changing in terms of time due to the charge leaking away through the sensitive membrane. Similarly to the capacitor, the floating gate is connected to the medium via the sensitive membrane (resistive layer), and a charge $Q_{FG}$ may initially be deposited. The charge leaking away from the floating gate results in a change in the potential or the voltage present at the control contact as compared to the source of the FET, a current between the source and a drain of the field-effect transistor is influenced. This source-to-drain current $I_{SD}$ may be used as a sensor current, for example.

With a potential measurement method, the current $I_{SD}$ between the drain and the source is measured at a constant voltage $U_{SD}$ between the source and the drain. Since the current $I_{SD}$ is a measure of the charge $Q_{FG}$ at the floating gate, as was explained above, the leakage rate $\Delta Q_{FG}$ of the charges (leakage) prior to and after binding or docking of analyte molecules to the membrane may therefore be measured.

In a further embodiment, one exploits the possibility of measuring, instead of the source-to-drain current $I_{SD}$, a threshold voltage shift $\Delta V_T$ or a gate voltage shift, specifically at a constant source-to-drain current $I_{SD}$ so as to thereby determine the charge $Q_{FG}$ at the floating gate. In a first approximation, the threshold voltage shift $\Delta V_T$ is proportional to the charge change $\Delta Q_{FG}$ and is given by $$\Delta V_T = \frac{\Delta Q_{FG}}{C_{Ox}}$$

($C_{Ox}$ being the capacitance of the gate oxide).

In a further embodiment, an EEPROM (electrically erasable programmable read-only memory) is used instead of the EPROM. Unlike the above-described EPROM, an EEPROM comprises an additional charge electrode (control gate electrode), via which the floating gate (sensor electrode) may be charged or discharged ("cleared"). An advantage of this embodiment is that it allows the possibility of several cyclic measurements which may be performed one after the other and wherein the floating gate is electrically charged or discharged via the control gate electrode.

Embodiments of the present invention also describe a method of measuring a concentration of an analyte while using a biosensor comprising an ion-sensitive membrane (resistive layer) and a sensor electrode (charge storage), measuring comprising a step of charging the sensor electrode when the ion-sensitive membrane is in contact with the medium. The method further comprises a step of changing an electrical resistance of the ion-sensitive membrane, the step of changing the resistance comprising docking of analyte molecules onto the ion-sensitive membrane. The method of measuring finally comprises a step of detecting a number of charges having passed the ion-sensitive membrane, the concentration of the analyte within the medium being determined from the number of charges.

The choice of the sensitive membrane is crucial for optimum operation of the embodiments and, thus, of the leakage sensor. The above-mentioned suitable selection of this membrane in this context relates to an achievable change in resistance upon contact of the membrane with the analyte. A potential sensitive membrane could be, for example, a lipid membrane, wherein the conductivity changes due to binding of analyte molecules due to the formation of ion channels along which a current may flow. In principle, by means of these and similar membranes, extremely low detection limits down to individual molecules may be achieved. Also, for optimum operation it is important to suppress further current paths between the sensor electrode and the reference electrode. This may be effected, for example, in that the sensor electrode (apart from the contact via the resistive layer) is otherwise electrically insulated from the medium.

Embodiments of the present invention thus represent an electrochemical biosensor, the operating principle and application possibilities of which differ from those of existing biosensors which are based on ion-selective electrodes (ISE) or on ion-sensitive field-effect transistors (ISFET). An ion-selective electrode essentially comprises an ion-selective membrane via which a concentration gradient of the specific type of ions may result, at equilibrium, when the ion-selective membrane is in contact with the medium for a certain time period taken for bringing about the equilibrium state. Here and in the following, the equilibrium state corresponds to a resistance value of the ion-selective membrane, said resistance value being constant in time and being achieved, for example, when the numbers of analyte molecules attaching to the membrane and being released again from the membrane are identical.

In contrast with the present invention, conventional biosensors are used for performing potentiometric measurements which generally measure the voltage of the ion-selective electrode relative to a reference electrode, which again is a measure of the analyte concentration (ion concentration) within the medium. These potentiometric measurements are effected instantaneously and detect the constant resistance value, arising in the equilibrium state, of the ion-sensitive membrane at a given point in time (for example via a voltage drop across the ion-sensitive membrane). To prevent interferences which are caused by further ions which may be present within the measurement solution (medium), the membrane should be selective toward only one type of ion, if possible. In practice, however, this is generally not entirely the case. A well-known example of an ISE is the pH glass electrode, which is selective toward $H^+$ ions. Further ISEs have been realized by using different membranes for different types of ions, such as $Na^+$, $K^+$, $NO_3^-$.

With a conventional ISFET (or even with different variations of CHEMFET, MEMFET, BIOFET, etc.), the field effect which results during docking of analyte molecules by means of, e.g., an inversion channel of a field-effect transistor, is exploited directly or in manner mediated by enzymes so as to generate a detection signal. Up to now, the field effect has been utilized particularly for realizing sensors for detecting DNA (deoxyribonucleic acid), but so far it has only been used as a pH sensor, since the operating principle of said sensors was not sufficiently understood.

Similarly to the ion-sensitive electrode, with the ISFET, docking of an analyte molecule is thus immediately ascertained as a detection signal, and thus fundamentally differs from the mode of operation of embodiments of the present invention. Specifically, embodiments describe a leakage sensor which enables, as an important feature, charging prior to measurement. Thus, factual signal amplification results as an advantage, since the actual act of detection, i.e. the attachment of the analyte molecule to the membrane, serves only as a trigger for discharge of the storage element (charge storage). Unlike with ISE or ISFET, the actual act of detection itself thus is not instantaneously converted to an electrical signal (which generally is small). The amplifying effect mentioned, however, takes up sufficient measuring time, which depends, in particular, on the measurement accuracy desired. With a relatively long waiting time or measuring time, a more precise result may be achieved, so that even minute amounts of analytes within the medium (and thus, an extremely small leakage rate of the charge stored) will add up to form a measurable effect. In this context, the measuring time may be at least one second or at least ten minutes, for example.

It is also possible, in further embodiments, to perform measurements with regard to different analytes by using different ion-sensitive membranes which are sensitive with regard to different analytes. Thus, the measuring procedure may be parallelized with regard to different analytes to be detected within the medium. In particular for blood tests, this fact may be exploited in that several constituents of the blood may be measured in parallel. Measurement of the leakage rate of the stored electrical charge on the charge storage may be performed continuously or discretely, continuous measurement referring to measuring the charge leaked away (voltage drop), and discrete measurement referring to a threshold value, for example, so that a signal is generated when a threshold value is exceeded. The time until the threshold value is reached may then be used, for example, as a measure of the concentration of the analyte within the medium. The threshold value may comprise, for example, a predefined threshold voltage shift of a field-effect transistor, the threshold voltage describing a voltage value which is present at the control contact (gate) of the field-effect transistor when the field-effect transistor transitions from the non-conductive to the conductive state (or vice versa). Strictly speaking, this transition does not occur instantaneously, but is a continuous process which, however, is effected within a highly limited range. During this process, the resistance changes considerably, and to give an even more precise definition of the above-described threshold value, one may use, for example, that voltage value wherein the resistance comprises a specific fraction ($1/2$ or $1/4$ or $1/10$) of said resistance present when the FET is in the conductive state.

In addition, embodiments are advantageous in the sense that they are based on a simple principle and offer vast possibilities of miniaturization, and thus have the potential of being integrated into microelectronic systems.

BRIEF DESCRIPTION OF THE DRAWINGS

Embodiments of the present invention will be detailed subsequently referring to the appended drawings, in which.

DETAILED DESCRIPTION OF THE INVENTION

With regard to the description which follows, it should be noted that in the different embodiments, functional elements which are identical or have identical actions have been designated by identical reference numerals, and that respective descriptions in the various embodiments represented below are interchangeable.

Figure 1:
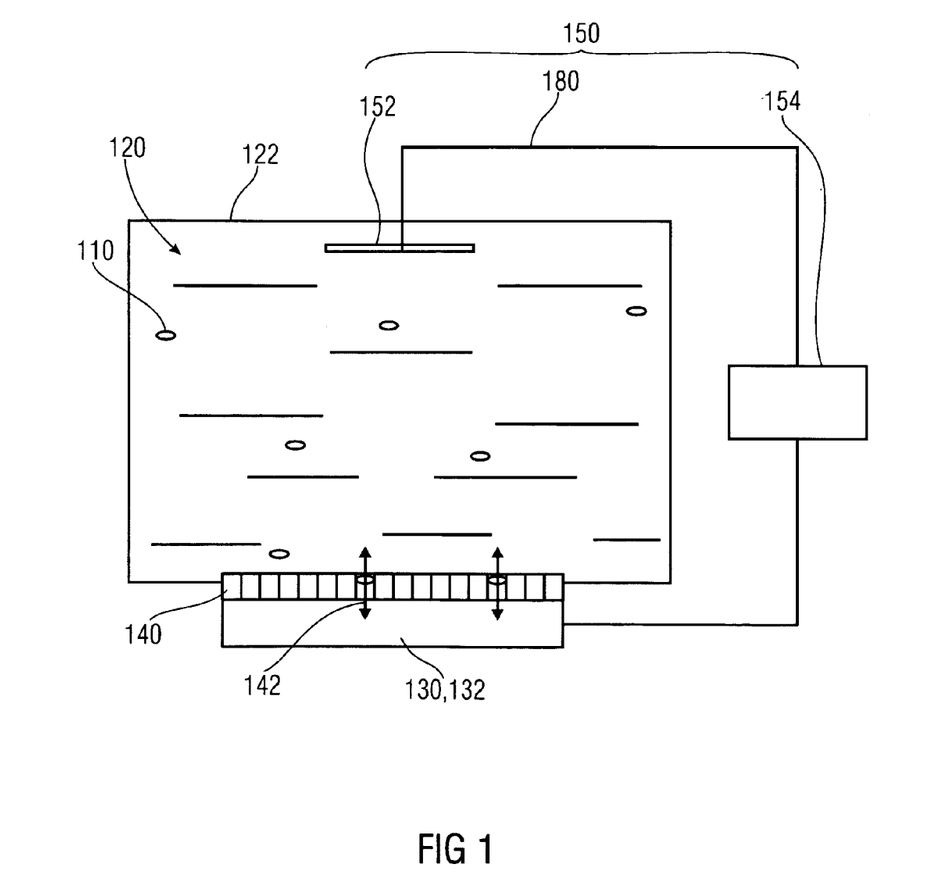
FIG. 1 shows a fundamental representation of an embodiment of the present invention.

FIG. 1 shows a schematic representation of an embodiment of a biosensor for measuring a concentration of an analyte 110 within a medium 120. The biosensor includes a charge storage 130 comprising a sensor electrode 132, the charge storage 130 and the sensor electrode 132 being depicted as one unit in FIG. 1. A resistive layer 140 is arranged between the charge storage 130, which comprises the sensor electrode 132, and the medium 120, it being possible to contact the resistive layer 140 with the medium 120. The resistive layer 140 is characterized in that its electrical resistance changes as a function of the concentration of the analyte 110, so that the electrical resistance of the resistive layer 140 will change once the resistive layer 140 has been contacted with the medium 120 and the analyte 110. After a while, a new constant resistance $R_A$ will again be established for the resistive layer 140. When this constant resistance value $R_A$ is present, the equilibrium state will have been achieved, and measurement of the concentration may begin.

In this context, measurement may be performed such that initially, the sensor electrode 132 in the charge storage 130 is charged, and that a means 150 for measuring an effect ascertains the amount of charge which has passed the resistive layer 140 within a period of time. The means 150 for measuring thus measures the effect of the charges 142 leaking away from the sensor electrode 132. For this purpose, the means 150 for measuring may comprise a reference electrode 152 and a control unit 154, which are connected to each other and to the charge storage via a connecting line 180. The control unit 154 may apply an output voltage $U_0$ between the reference electrode 152 and the sensor electrode 132 by means of a voltage source, for example, application of the voltage $U_0$ corresponding to application of charges to the sensor electrode 132. Application (or removal) of the corresponding charges to the sensor electrode 132, however, generally is not effected via charges passing through the membrane, but advantageously is effected via a further contact (not shown in FIG. 1)—either directly or via tunneling through an insulating layer.

Once the equilibrium state has been established, so that the resistive layer 140 comprises a resistance value $R_A$ which is constant in time (but has changed), the control unit 154 may isolate, for example, the reference electrode 152 and the sensor electrode 132 from the voltage source, and may measure, after a predefined time period, a remaining voltage $U_A$ between the reference electrode 152 and the sensor electrode 132. The difference between the remaining electrical voltage $U_A$ and the original output voltage $U_0$ will then correspond to a leakage rate of charge carriers 142 having passed the resistive layer 140, and is thus a measure of the changed resistance value $R_A$ of the resistive layer 140. By means of a reference measurement of the resistance value $R_0$ of the resistive layer 140, wherein the resistive layer 140 is exposed to a medium 120 comprising no analyte 110, it may be ascertained how strongly the resistance value of the resistive layer 140 has changed in the presence of or during contact with the analyte 110, and is thus a measure of the concentration of the analyte 110 within the medium 120.

In the schematic representation of FIG. 1, the medium 120 is arranged within a container 122, but the shape and the implementation of the container 122 may be varied. In addition, it is possible that the charge storage 130 comprising the resistive layer 140 is arranged within a replaceable unit comprising a detachable connection to the container 122, so that different analytes 110 may be measured by a replacement of this replaceable unit. This will be the case, for example, when the different replaceable units comprise different resistive layers which are sensitive with regard to different analytes.

Figure 2:
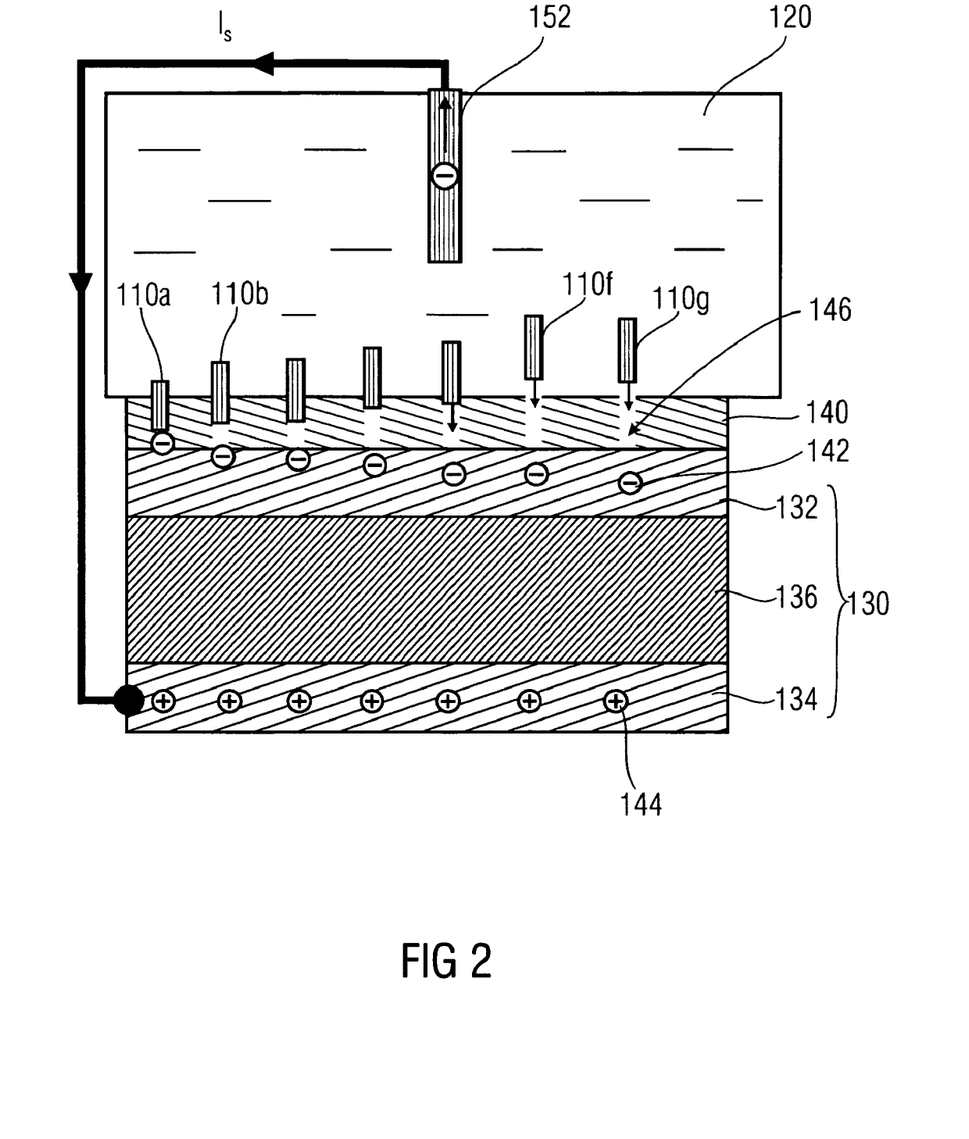
FIG. 2 shows a schematic cross-sectional representation of a biosensor using a capacitor.

FIG. 2 shows a schematic representation of a biosensor, wherein the charge storage 130 is formed by a capacitor. The charge storage 130 thus comprises the sensor electrode 132, a further electrode 134 and a dielectric layer 136, the dielectric layer 136 electrically isolating the sensor electrode 132 and the further electrode 134. The resistive layer 140, onto which (as is schematically shown in FIG. 2) the analyte molecules 110a, 110b, . . . , 110f, 110g dock, is arranged on the sensor electrode 132. In this context, docking is effected at binding sites 146 of the resistive layer 140 which are selective with regard to the analyte molecules 110, as a result of which the resistance value of the resistive layer 140 changes. At the time when the number of analyte molecules 110 which have docked onto the resistive layer 140 no longer changes, and is constant, the resistance value of the resistive layer 140 also becomes constant, and the above-described equilibrium state will have been established.

By means of the means 150 for measuring, a voltage $U_0$ is then applied to the charge storage 130, so that, as is shown in FIG. 2, for example, negative electrical charges 142 are applied to the sensor electrode 132, and, at the same time, positive electrical charges 144 are applied to the further electrode 134. After application of the charges, the means 150 for measuring may isolate the charge storage (in FIG. 2, capacitor) from the voltage source. At the same time, the further electrode 134 may become connected or already be connected to the reference electrode 152, so that a potential gradient will form between the sensor electrode 132 and the reference electrode 152 and will result in current flowing between the sensor electrode 132 and the reference electrode 152 by passing the resistive layer 140 and by passing the medium 120. The charge transfer through the resistive layer 140 may be effected, for example, along ion channels, which may be formed, for example, by the docking of the analyte molecules 110 within the resistive layer 140. As is described in FIG. 1, the current (leakage current $I_S$) depends on the resistance value $R_A$ of the resistive layer 140. Since the resistance value $R_A$ depends on the number of the docked analyte molecules 110 or, for example, on the number of ion channels forming, the concentration of the analyte molecules 110 within the medium 120 may thus be determined by measuring the leakage current $I_S$ or, even better, by measuring the effect of the leakage current flowing from the sensor electrode 132 to the reference electrode 152.

Passage of the electrical charges through the resistive layer 140 can take place, for example, in the following way. The analyte molecules 140 comprise an affinity toward the resistive layer 140, and the resulting binding alters the conductivity of the resistive layer 140 by opening ion channels. Ions from the medium can enter, e.g., the ion channels in the direction of the sensor electrode 132, and charges present on the sensor electrode 132 will couple to the ions and hence cause an effective electric current from the sensor electrode 132 into the medium (e.g. using the ions as a carrier). Hence, the analyte molecules within the medium act, in a sense, as a switch for opening the ion channels, which enables the ion-mediated current (the charges do not enter the medium directly, but will be bound to the ions). This results in said charge leakage. This effect occurs also in certain biological membranes, which are permeable to specific ions only in the presence of a membrane-specific protein.

FIG. 2 schematically shows a charge carrier transfer in the form of negatively charged charge carriers 142 which are shown, for one thing, on the sensor electrode 132 and on the reference electrode 152, and which further result in the capacitor 130 being discharged. Since this current $I_S$ (leakage current or sensor current) will generally be very small, it is advantageous not to perform a potential measurement until the end of a predetermined time period, in the course of which the charge state of the capacitor (charge storage 130) may be ascertained.

In other words, the sensor mechanism of the leakage sensor, as is shown in FIG. 2, may be summarized such that electrical charges are initially stored—e.g. onto capacitor plates (the sensor electrode 132 and the further electrode 134), which may comprise, for example, a metallic material. The membrane 140, which may also be implemented as a coating, may be deposited onto the upper capacitor electrode (the sensor electrode 132), and may be connected to the lower capacitor plate (further electrode 134) via an electrolyte (medium 120 comprising analyte 110) and the reference electrode 152. During docking of an analyte 110, the conductivity of the membrane (resistive layer 140) may increase, and at the same time, the charge leaking away from the capacitor electrode (sensor electrode 132) may also increase. To be able to detect a specific analyte 110 within a matrix comprising various components, the membrane should have selective binding sites 146 for this analyte 110. Binding of the analyte molecules 110 to the binding sites 146 may occur, for example, in the absence of a voltage or of any other external electromagnetic field.

Figure 3:
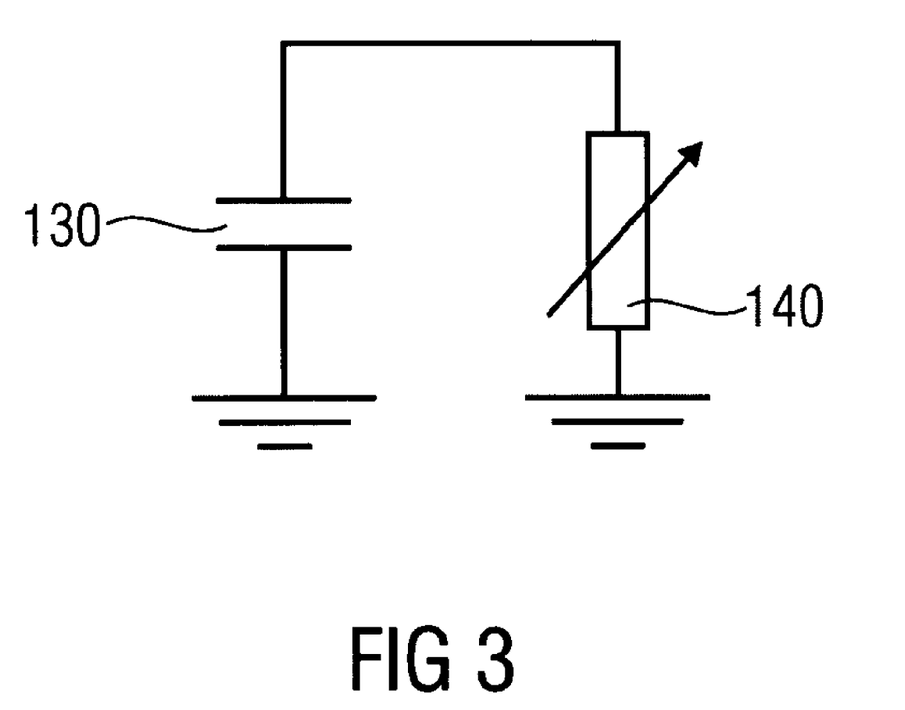
FIG. 3 shows an equivalent circuit diagram of the embodiment of the biosensor using a capacitor.

FIG. 3 shows an idealized equivalent circuit diagram of a biosensor (leakage sensor), wherein the charge storage 130 (charge-storing element) is given, for example, by a capacitor, an EPROM, or the like, and wherein, in addition, the resistive layer 140 is represented by a variable resistor connected in parallel. All remaining current paths for further leakage currents are neglected here, and are consequently not shown; the variable resistor 140 only symbolizes that the resistance value of the resistive layer or membrane 140 (sensitive sensor layer) changes upon binding or docking of analyte molecules.

Figure 4:
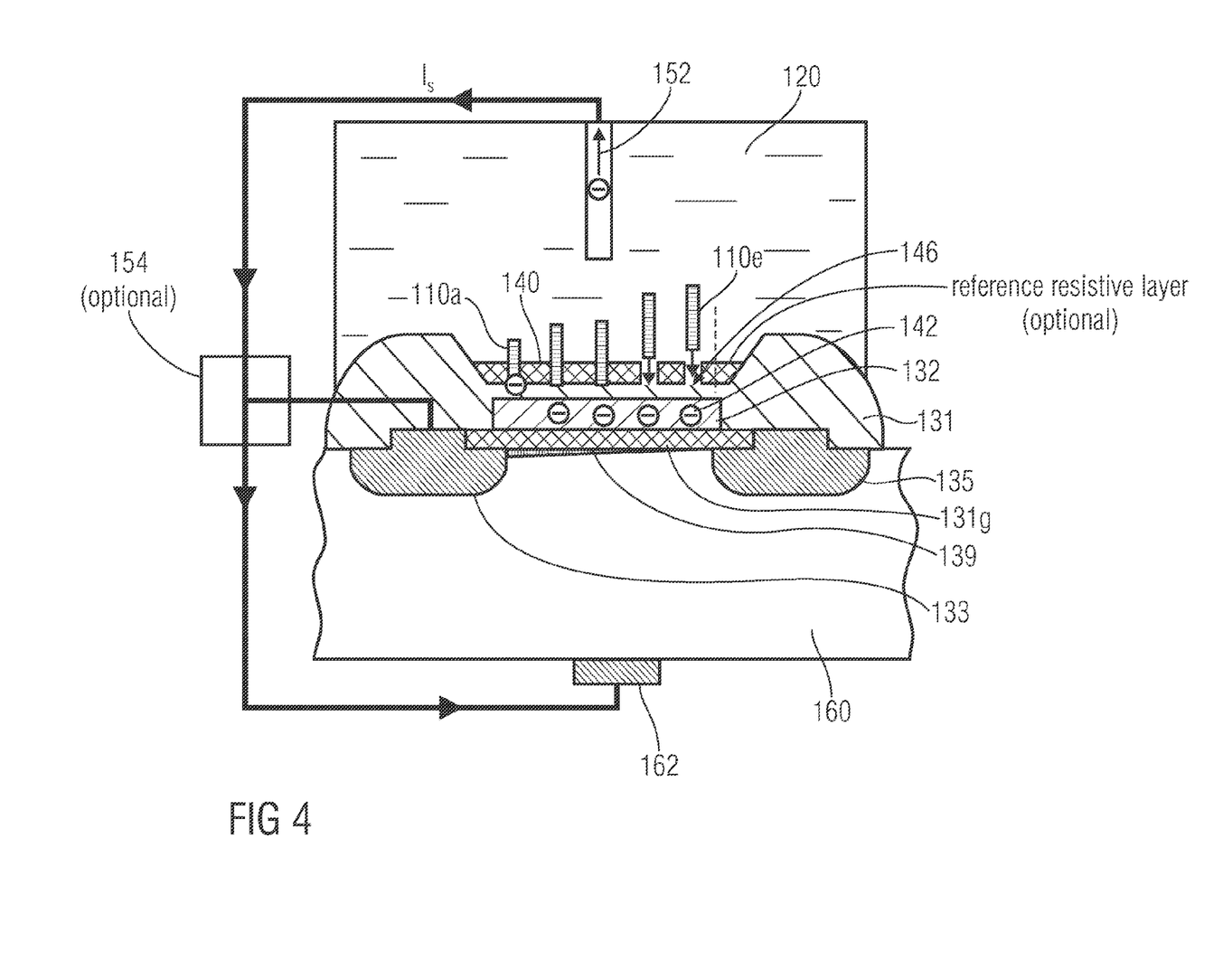
FIG. 4 shows a schematic representation of an embodiment using an EPROM.

FIG. 4 shows a further embodiment wherein the charge storage 130 is given by an EPROM. According to this, the sensor electrode 132 in these embodiments is designed as a floating gate, a floating gate being a control terminal for a field-effect transistor which is electrically insulated from the surroundings by a dielectric 131 (dielectric layer), and is arranged above a channel area 139 of the field-effect transistor. The floating gate 132 is isolated from the channel region 139 by a gate oxide 131g. The field-effect transistor further comprises source and drain areas or terminals 133, 135 between which the channel area 139 may form. The source and drain areas 133 and 135 are implemented within a substrate 160 which comprises the dielectric 131 on a first main side, and comprises a body contact 162 on an opposing main side.

The body contact 162 may be electrically connected, for example, to the source area 133 or to a source electrode. Thus, the dielectric layer 131 is formed, on the first main side of the substrate 160, between the source area 133 and the drain area 135, the dielectric layer 131 electrically insulating the sensor electrode 132 (floating gate) both from the substrate 160 and from the resistive layer 140 arranged on the dielectric layer 131. The resistive layer 140 in turn comprises analyte-specific binding sites 146 designed to allow the analyte 110 to be detected to dock or to establish a binding, which in turn results in a change in the electrical resistance of the resistive layer 140. FIG. 4 shows, by way of example, five analyte molecules 110a, ..., 110e, which dock onto the resistive layer 140. As was described before, in this case, too, an equilibrium state will establish itself after a while, wherein the number of analyte molecules 110 docked onto the resistive layer 140 is equal to the number of analyte molecules being released from the resistive layer 140.

In further embodiments, no insulating layer 131 is formed between the floating gate 132 and the resistive layer 140, so that the resistive layer 140 obtains direct contact with the floating gate 132. The formation of the insulating layer 131 between the floating gate 132 and the resistive layer 140, however, is compatible with CMOS technology, and is therefore advantageous.

In the embodiment of FIG. 4, the reference electrode 152 comprises an electrical contact with the source terminal 133 and to the body contact 162, along both of which a sensor current $I_S$ forms during a sensor operation, the sensor current $I_S$ again corresponding to a leakage current which leads to the floating gate (sensor electrode 132) being discharged. In this embodiment, however, discharge of the sensor electrode 132 is effected via a tunnel effect, wherein electrical charges 142 from the sensor electrode 132 initially pass the dielectric layer 131 formed between the sensor electrode 132 and the resistive layer 140. Subsequently, the electrical charges pass the resistive layer 140 and the medium 120 so as to reach the reference electrode 152. While passing the resistive layer 140, the charge transfer again may occur, for example, along ion channels which are formed as a result of the analyte molecules 110 docking onto the resistive layer 140.

Thus, the principle of this embodiment may also be summarized as follows. The EPROM is a "floating gate" device, wherein a dielectric 131 electrically insulates the so-called floating gate 132 from the surroundings, so that an electrically insulated electrode is formed. In addition, the electrically insulated floating gate 132 is situated above the inversion channel (channel region 139) located between the semiconductor substrate 160 and the doped areas of the source terminal 133 and the drain terminal. Charge 142 may be applied to the floating gate 132, for example by means of a tunnel effect. The charge 142 applied to the floating gate 132 results, for example, in a formation of an inversion channel due to the field effect influence, and thus influences the current between the source region 133 and the drain region 135. This influence may occur either by narrowing or enlarging the channel area 139. The source-to-drain current $I_{SD}$, which utilizes the existing channel area 139, is either reduced, or amplifies, and is therefore a measure of the charge quantity on the floating gate

132. In the embodiment which is shown here of a leakage sensor comprising an EPROM, the selective membrane (resistive layer 140), the conductivity of which changes due to docking of analyte molecules, is located above the floating gate 132. Thus, the leakage rate with regard to the underlying floating gate 132 will also change. So that the charge 142 may leak away from the floating gate 132, the matrix (medium 120) is connected to analytes 110 (which generally are present as an aqueous solution), to a reference electrode 152, to the source area 133, and to the body contact 162.

Figure 5:
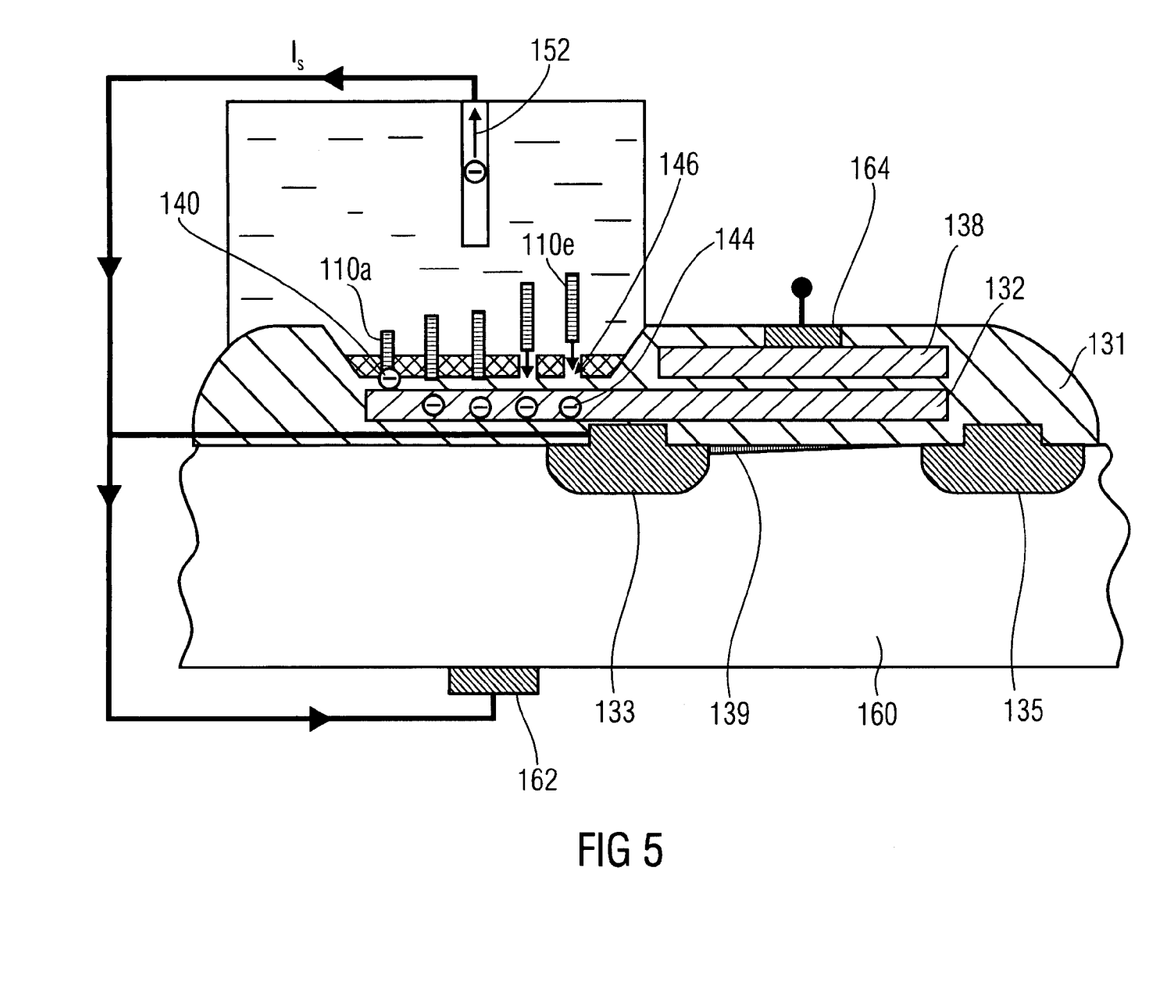
FIG. 5 shows a schematic representation of an embodiment using an EEPROM.

FIG. 5 shows a schematic representation of a further biosensor in the form of a leakage sensor using an EEPROM. In this embodiment, too, the biosensor is implemented on a substrate 160, the substrate 160 comprising a source area 133 and a drain area 135 on a main side of the substrate 160, between which a channel area 139 may form. A side which is opposite the main side in turn has a body contact 162 formed thereon, which in the embodiment as is shown in FIG. 5 is connected to the source area 133. In addition, the main side has a dielectric layer 131 arranged thereon, within which, in turn, a sensor electrode 132 (floating gate) is located. Also, the biosensor comprises a control gate electrode 138 (control electrode) connected to a control terminal 164. The control gate electrode 138 is isolated from the channel area 139 by a layer sequence, the layer sequence comprising the sensor layer 132 (sensor electrode) isolated from the dielectric layer 131, such that the sensor electrode 132 is electrically insulated both from the channel area 139 and from the control gate electrode 138 by the dielectric layer 131. In addition, the sensor electrode 132 is implemented such that it extends into a further substrate area. In the further substrate area, the substrate 160 has the dielectric layer 131, the sensor electrode 132 and the resistive layer 140 arranged thereon such that the sensor electrode 132 is electrically insulated both from the substrate 160 and from the resistive layer 140 by the dielectric layer 131.

By applying a voltage or a potential to the control gate electrode 138, in this embodiment the sensor electrode 132 may be charged (e.g. while exploiting the tunnel effect), so as to subsequently remove the potential (voltage source) from the control gate electrode 138. Charging the sensor electrode 132 either results in that a channel region 139 will form, or in that (depending on the doping selected) a channel region 139 is narrowed. As with the embodiments described above, docking of analyte molecules 110 onto analyte-specific binding sites 146 of the resistive layer 140 (ion-sensitive membrane) results in that the resistance value of the resistive layer 140 changes—if it is in contact with the medium 120 comprising the analytes 110. By way of example, FIG. 5 shows a total of five analyte molecules 110a, . . . , 110e.

In addition, the embodiment in FIG. 5 again comprises a reference electrode 152, so that a sensor current $I_S$ may form, the sensor current $I_S$ including charge carriers which tunnel through the dielectric layer 131 from the sensor electrode 132 and which pass the resistive layer 140 comprising the analyte molecules 110a to 110e, and which finally reach the reference electrode 152 via the medium 120. From there, they are transferred on to the source area 133, for example, which in its turn is connected to the body contact 162. This results in that the current $I_{SD}$ between the source area 133 and the drain area 135 changes, specifically due to a change in the potential at the source terminal 133 and due to a change in the charge carrier density on the sensor electrode 132, which in turn changes the formation of the channel region 139. Since the sensor electrode 132 corresponds to a common gate (control terminal) of a FET, the change in the source-to-drain current $I_{SD}$ is a consequence of the change in the gate-to-source voltage $U_{GS}$.

The embodiment shown in FIG. 5 is particularly advantageous in that it offers, via the control gate electrode 138, the possibility of quickly recharging the sensor electrode 132, and thus enables cyclic measurement.

In the embodiments as are shown in FIG. 4 and FIG. 5, it shall further be noted that the layer thickness of the dielectric layer 131 between the sensor electrode 132 and the underlying substrate and between the sensor electrode 132 and the resistive layer 140 is selected such that for one thing, a channel region 139 will change as a result of a charge-carrier change ΔQ on the sensor electrode 132, and that charge carriers from the sensor electrode 132 may pass the dielectric layer 131 via the tunnel effect, and may reach the resistive layer 140. For example, if the dielectric layer 131 between the sensor electrode 132 and the resistive layer 140 is selected to be too thick, the tunnel effect of charge carriers between the sensor electrode 132 and the resistive layer 140 will be very heavily suppressed, so that the sensor current $I_S$ will also be clearly reduced. Thus, the sensitivity would also decrease. In accordance with the invention, the sensor current $I_S$ is not detected directly, but rather its effect (e.g. a charge quantity leaking away from the sensor electrode 132 after a time interval).

The illustrated connections in the embodiments of FIGS. 2, 4 and 5 may generally be varied further and comprise further circuit devices. For example, as is shown in FIG. 1, a control unit 154 may optionally exist which may realize various connections and may additionally provide a current and/or voltage supply. For example, the control unit 154 may also be connected to the drain area 135, to a ground where, for example, the source area 133 is present, and to the control electrode 138. With flawless functioning, it is also to be noted that the sensor electrode 132 has no direct contact with the medium 120 comprising the analytes 110, since otherwise the exploited effect of a change in resistance of the resistive layer 140 as a result of the presence of analytes 110 will be bridged and will not be measurable.

In further embodiments, the sensitive membrane may also be structured such that it is not any docking of the analyte 110 that leads to a change in resistance, but that rather the analyte 110 dissolves constituents out of the membrane, and that a change in resistance is effected in this manner.

Embodiments of the present invention therefore solve the following problems which arise when using conventional biosensors, and thus exhibit advantages over conventional methods.

(a) A highly sensitive biosensor may be realized using the inventive concept, since precharging of the sensor electrode 132 or of the charge storage 130 may be arbitrarily adjusted within certain technological limits, and since thus, a large change ΔQ in the charge is to be expected after the charge has leaked off via the resistive layer 140. Even a very small change in the conductivity of the resistive layer 140 would result, with a sufficiently long waiting time, in a large change ΔQ in the charge. It would also be advantageous in this context to select a membrane such that the conductivity is as small as possible in the absence of the analyte, and increases, in the presence of the analyte, so much that the charge-storing element (charge storage 130) discharges measurably faster than in the absence of the analyte 110.

(b) A highly selective biosensor may also be realized in that a membrane 140 is used which is modeled on the basis of natural cell membranes, and which thus exhibits very high selectivity with regard to specific analytes 110. Thus, a very selective membrane 140 may be formed, which in turn has a large influence on the measurement effect.

(c) Moreover, in dependence on the charge-storing element used (capacitor, EEPROM, EPROM and others), a high potential is to be expected with regard to miniaturization of the leakage sensor or biosensor. Due their ability to be integrated into microelectronic circuits (e.g. on a CMOS basis), the above-described embodiments of a capacitor, EPROM or EEPROM further offer excellent prerequisites for an extremely high ability of a biosensor to be miniaturized. In particular, the biosensor may be part of an integrated circuit (MOS or CMOS).

(d) Finally, the biosensor is very easy to operate. The simplicity of handling results, for example, from the fact that the measuring procedure comprises established electrical measurements, and that expensive washing steps or the like may be dispensed with.

Embodiments may further be modified in that a different mechanism is employed for the leakage of charges from the charge storage 130. One example could be UV light.

In addition, one possibility consists in using several biosensors which may be arranged in an array, for example. Instead of a leakage of charges, charging of the sensor electrode 132 may be exploited, and, for example, a point in time may be measured by which the sensor electrode 132 has become fully charged.

Further embodiments also comprise a reference resistive layer, which may also be contacted with the medium, the reference resistive layer comprising no selective binding sites for the analyte, however. In this manner, for example, differential measurement becomes possible, so that the sensitivity for the analyte may be increased.

An important feature of embodiments of an inventive biosensor is given by the fact that a charge storage 130, in whichever form it may be realized, is charged prior to the actual act of detection and is utilized for the purpose of measuring discharge of the charge storage 130 as an act of detection. Thus, embodiments of analyzing substances are applicable in biochemical industry, but they may also be employed in food inspection. In particular in clinical diagnostics, an inventive biosensor may be employed, for example, for analyzing a blood serum for signs of disease, or may be employed in early tumor diagnosis.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A biosensor for measuring a concentration of an analyte within a medium, comprising:
    an electrical charge storage, the electrical charge storage comprising a sensor electrode;
    a resistive layer comprising an electrical resistance which changes upon contact with the analyte, and
    a measurer coupled to the electrical charge storage for measuring an effect of electrical charges stored in the electrical charge storage or passing between the electrical charge storage and the medium;
    wherein the resistive layer is contacted with the medium and is arranged between the medium and the sensor electrode such that during contact with the medium, electrical charges stored in the electrical charge storage prior to the contact are passed between the electrical charge storage and the medium through the resistive layer at a rate determined by the electrical resistance of the resistive layer, wherein a change in a number of electrical charges stored by the electrical charge storage over a period of time is determined by the measurer to measure the concentration of the analyte.

2. The biosensor as claimed in claim 1, further comprising an integrated circuit, and wherein the electrical charge storage is integrated into the integrated circuit.

3. The biosensor as claimed in claim 1, wherein the sensor electrode is electrically insulated from the medium by the resistive layer except for one electrical connection.

4. The biosensor as claimed in claim 1, wherein the charge storage comprises a capacitor, the capacitor comprising the sensor electrode and a further electrode which are isolated by a dielectric layer, and the resistive layer being isolated from the dielectric layer by the sensor electrode.

5. The biosensor as claimed in claim 1, wherein the measurer comprises a reference electrode.

6. The biosensor as claimed in claim 1, wherein the resistive layer is implemented to exhibit a lower resistance during contact with the analyte.

7. The biosensor as claimed in claim 1, wherein the measurer comprises a control unit, and the control unit is implemented to measure a voltage or a current between a reference electrode and the sensor electrode.

8. The biosensor as claimed in claim 7, wherein the control unit is implemented to apply a predetermined charge quantity to the sensor electrode by applying a voltage source, and to subsequently interrupt a connection between the sensor electrode and the voltage source.

9. The biosensor as claimed in claim 8, wherein the control unit is implemented to determine, after a predetermined time period, a remaining charge quantity on the sensor electrode.

10. The biosensor as claimed in claim 9, wherein the control unit is implemented to initially apply an output voltage $U_0$ between the reference electrode and the sensor electrode via a connection and to subsequently release the connection,
    and wherein the control unit is implemented to determine, after a predetermined time period, a residual voltage $U_A$ and to determine the concentration of the analyte within the medium from a ratio of the residual voltage $U_A$ to the output voltage $U_0$.

11. The biosensor as claimed in claim 1, wherein the resistive layer comprises selective binding sites, the selective binding sites being implemented to selectively bind the analyte so as to thereby change the electrical resistance of the resistive layer by a predetermined value.

12. The biosensor as claimed in claim 11, further comprising a reference resistive layer exhibiting a reference resistance which remains the same upon contact with the analyte.

13. The biosensor as claimed in claim 11, wherein the predetermined value is at least 5%.

14. The biosensor as claimed in claim 11, wherein the selective binding sites are implemented to bind analyte molecules from a matrix.

15. The biosensor as claimed in claim 1, wherein the resistive layer comprises a lipid membrane.

16. The biosensor as claimed in claim 1, wherein the charge storage comprises
    a source area; and
    a drain area,
        the source area and the drain area being isolated by a channel area comprising a channel resistance,
        and the channel area being isolated from the sensor electrode by an insulating layer, so that a change in the number of charges on the sensor electrode results in a change in the channel resistance.

17. The biosensor as claimed in claim 16, wherein a further part of the insulating layer is arranged between the sensor electrode and the resistive layer, so that the stored electrical charges from the sensor layer reach the resistive layer by means of tunneling through the further part of the dielectric layer.

18. The biosensor as claimed in claim 16, comprising a control unit and wherein a body contact of the charge storage, the source area and the drain area are electrically connected to the control unit.

19. The biosensor as claimed in claim 18, wherein the control unit is implemented to measure, at a constant voltage between the source area and the drain area, a current between the source area and the drain area, and to determine a concentration of the analyte within the medium from a temporal change in the current.

20. The biosensor as claimed in claim 19, wherein the control unit is implemented to determine a threshold voltage shift due to a change in the number of electrical charges stored on the sensor electrode,
and wherein the control unit is further implemented to determine the concentration of the analyte within the medium from the threshold voltage shift.

21. The biosensor as claimed in claim 1, wherein the charge storage comprises
a source area;
a drain area;
a channel area formed between the source area and the drain area on a first main surface of the substrate; and
a control electrode,
an insulating layer, which electrically insulates the sensor electrode from the channel area, being formed on the first main surface of the substrate,
and the control electrode being arranged on a side of the sensor electrode which faces away from the channel area, and being electrically insulated from same by a further part of the insulating layer,
and the sensor electrode extending along the channel area and along a further substrate area, the sensor electrode in the further substrate area being electrically insulated from the substrate and from the resistive layer by the insulating layer.

22. The biosensor as claimed in claim 21, further comprising a reference electrode, and wherein the reference electrode is contacted with the medium, and
wherein a body contact is implemented on the side which is opposite the main side of the substrate, the body contact and the source area and the reference electrode being electrically connected.

23. The biosensor as claimed in claim 22, further comprising a control unit, and wherein the control unit is electrically connected to the reference electrode and the drain area and the control electrode.

24. The biosensor as claimed in claim 21, wherein the control electrode and the insulating layer are implemented to charge or discharge the sensor electrode by tunneling charge carriers through the insulating layer, so that the number of electrical charges stored on the sensor electrode changes.

25. The biosensor as claimed in claim 23, wherein the control unit is implemented to repeatedly charge or discharge the sensor electrode so as to perform repeated measurements of the concentration of the analyte within the medium.

26. The biosensor as claimed in claim 1, wherein a further substrate region comprises a further resistive layer,
the further resistive layer comprising a selective membrane for a further analyte within the medium, so that the resistive layer and the further resistive layer are selective with regard to different analytes, so that upon contact with the medium, a change in an electrical resistance of the further resistive layer depends on a concentration of the further analyte within the medium.

27. The biosensor as claimed in claim 1, wherein the measurer is implemented to detect charging of the sensor electrode or leakage of electrical charges away from it.

28. A method of producing a biosensor for measuring a concentration of an analyte within a medium, comprising:
providing a charge storage comprising a sensor electrode;
applying to the sensor electrode a resistive layer comprising an electrical resistance which changes upon contact with the analyte,
providing a measurer coupled to the charge storage for measuring an effect of electrical charges stored in the charge storage or passing between the charge storage and the medium;
the resistive layer being arranged such that it is contacted with the medium and is arranged between the medium and the sensor electrode such that during contact with the medium, electrical charges stored in the charge storage prior to the contact are passed between the charge storage and the medium through the resistive layer at a rate determined by the electrical resistance of the resistive layer; and
determining by the measurer a change in a number of electrical charges stored by the electrical charge storage over a period of time to measure the concentration of the analyte.

* * * * *